(12) United States Patent
Eck et al.

(10) Patent No.: US 6,433,222 B1
(45) Date of Patent: Aug. 13, 2002

(54) METHOD FOR PRODUCING ACRYLIC ACID

(75) Inventors: Bernd Eck, Viernheim; Jörg Heilek, Bammental; Volker Schliephake, Schifferstadt; Theo Proll, Bad Dürkheim; Klaus Bröllos, Seeheim-Jugenheim; Otto Machhammer, Mannheim; Joachim Thiel, Neustadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/764,985

(22) PCT Filed: Jul. 21, 1999

(86) PCT No.: PCT/EP99/05204

§ 371 (c)(1),
(2), (4) Date: Jan. 22, 2001

(87) PCT Pub. No.: WO00/05188

PCT Pub. Date: Feb. 3, 2000

(30) Foreign Application Priority Data

Jul. 22, 1998 (DE) .......................... 198 33 049

(51) Int. Cl.$^7$ .............................. C07C 51/42
(52) U.S. Cl. ............... 562/600; 562/600; 562/545
(58) Field of Search ................... 562/600, 545

(56) References Cited

U.S. PATENT DOCUMENTS

| | | |
|---|---|---|
| 3,198,750 A | 8/1965 | Callahan et al. |
| 3,736,355 A | 5/1973 | Croci et al. |
| 3,798,264 A | 3/1974 | Kubota et al. |
| 3,865,873 A | 2/1975 | Oda et al. |
| 3,932,500 A | 1/1976 | Duembgen et al. |
| 4,110,370 A | 8/1978 | Engelbach et al. |
| 4,219,389 A * | 8/1980 | Biola et al. |
| 4,224,187 A | 9/1980 | Vanderspurt |
| 4,780,568 A * | 10/1988 | Pascoe et al. |
| 5,426,221 A | 6/1995 | Willersinn |
| 5,510,558 A | 4/1996 | Umansky et al. |
| 5,705,684 A | 1/1998 | Hefner et al. |

FOREIGN PATENT DOCUMENTS

| | | |
|---|---|---|
| DE | 0675100 A2 * | 10/1995 |
| EP | 0 117 146 | 8/1984 |
| EP | 0 253 409 | 1/1988 |
| EP | 0 257 565 | 3/1988 |
| EP | 0 293 224 | 11/1988 |
| EP | 0 551 111 | 7/1993 |
| EP | 0 608 838 | 8/1994 |
| EP | 0 675 100 | 10/1995 |
| GB | 1 450 986 | 9/1976 |
| GB | 2 146 636 | 4/1985 |
| JP | 45-32417 | 10/1970 |
| JP | 7-118966 | 5/1971 |
| JP | 7-118968 | 5/1971 |
| JP | 7-241885 | 10/1972 |
| JP | 58-140039 | 8/1983 |
| JP | 7-082210 | 3/1995 |
| JP | 7-118766 | 5/1995 |
| JP | 40915721 A * | 6/1997 |

OTHER PUBLICATIONS

F. Cavani, et al., Catalysis Today, vol. 24, pp. 307–313, "The Oxidative Dehydrogenation of Ethane and Propane as an Alternative Way for the Production of Light Olefins", 1995.

* cited by examiner

*Primary Examiner*—Gary Geist
*Assistant Examiner*—Farhad Forohar
(74) *Attorney, Agent, or Firm*—Oblon, Spivak, McClelland, Maier & Neustadt, P.C.

(57) ABSTRACT

A process for the preparation of acrylic acid by:
(a) preparation of a gaseous product mixture which essentially has the composition of a reaction mixture of catalytic gas-phase oxidation of $C_3$-alkanes, $C_3$-alkenes, $C_3$-alkanols and/or $C_3$-alkanals and/or intermediates thereof to acrylic acid, which comprises
(b) condensation of the gaseous product mixture,
(c) crystallization of the acrylic acid from the solution obtained in stage (b), with partial evaporation of the solution under reduced pressure,
(d) isolation of the resulting crystals from the mother liquor,
(e) recycling of at least a part of the mother liquor from stage (d) to stage (b) and
(f) recycling of at least a part of the evaporated solution from stage (c) to stage (b).

20 Claims, 1 Drawing Sheet

METHOD FOR PRODUCING ACRYLIC ACID

Figure 1:
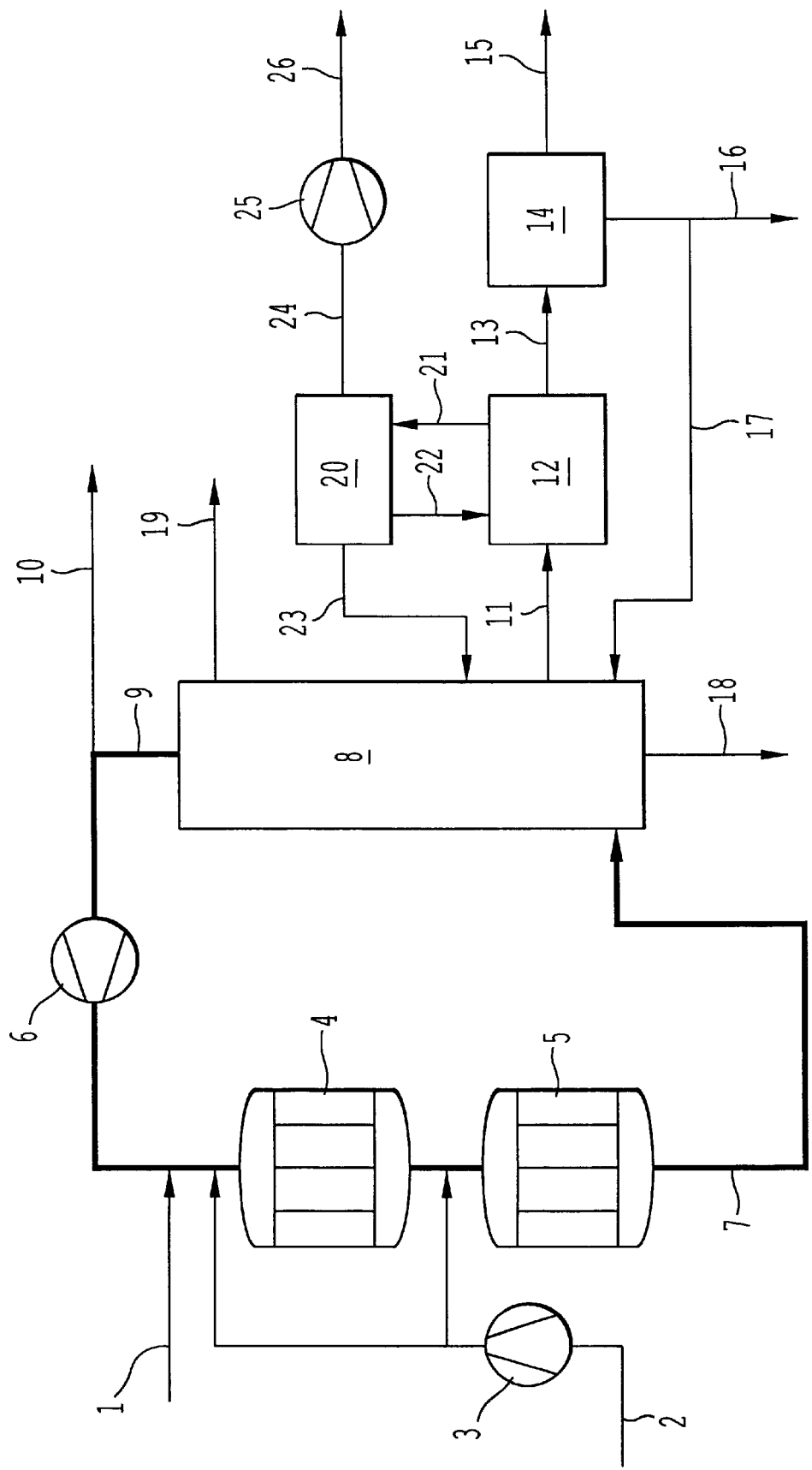

The present invention relates to a process for the preparation of acrylic acid.

Acrylic acid is an important key chemical. Owing to its very reactive double bond and the acid function, it is particularly suitable as a monomer for the preparation of polymers. Of the amount of acrylic acid monomers produced, the major part is esterified before the polymerization—to give, for example, adhesives, dispersions or surface coatings. Only the minor part of the acrylic acid monomers produced is polymerized directly—to give, for example, "superabsorbers". Whereas monomers of high purity are generally required in the direct polymerization of acrylic acid, the requirements regarding the purity of acrylic acid are not so high when they are esterified before the polymerization.

It is generally known that acrylic acid can be prepared by gas-phase oxidation of propene with molecular oxygen under heterogeneous catalysis over catalysts present in the solid state at from 200 to 400° C. in one stage or two stages via acrolein (cf. for example DE-A-1 962 431, DE-A-2 943 707, DE-C-1 205 502, DE-A-195 08 558, EP-A-0 257 565, EP-A-0 253 409, DE-A-2 251 364, EP-A-0 117 146, GB-B-1 450 986 and EP-A-0 293 224). Here, oxidic multicomponent catalysts, for example based on oxides of the elements molybdenum, bismuth and iron (in the 1st stage) or molybdenum and vanadium (in the 2nd stage) are used.

DE-C-2 136 396 discloses the separation of the acrylic acid from the reaction gases obtained in the catalytic oxidation of propene or acrolein by countercurrent absorption with a mixture of about 75% by weight of diphenyl ether and about 25% by weight of biphenyl. Furthermore, DE-A-2 449 780 discloses the cooling of the hot reaction gas by partial evaporation of the solvent in a direct condenser (quench apparatus) before the countercurrent absorption. What is problematic here and in further process steps is that solids are obtained in the apparatuses, reducing the availability of the plant. According to DE-A-4 308 087, the production of these solids can be reduced by adding a polar solvent, such as dimethyl phthalate in an amount of from 0.1 to 25% by weight to the relatively nonpolar solvent mixture comprising diphenyl ether and biphenyl.

In addition to the absorption, described above, of the acrylic acid-containing reaction product into a high-boiling solvent mixture, other known processes provide total condensation of acrylic acid and of the water of reaction furthermore formed in the catalytic oxidation. This gives an aqueous acrylic acid solution which can be further worked up by distillation with an azeotropic agent (cf. DE-C-3 429 391, JP-A-1 124 766, JP-A-7 118 766, JP-A-7 118 966-R, JP-A-7 118 968-R, JP-A-7 241 885) or by an extraction method (cf. DE-A-2 164 767, JP-A-5 81 40-039 and JP-A-4 80 91 013). In EP-A-0 551 111 the mixture of acrylic acid and byproducts which is prepared by means of catalytic gas-phase oxidation is brought into contact with water in an absorption tower, and the resulting aqueous solution is distilled in the presence of a solvent which forms an azeotropic mixture with polar low boilers, such as water or acetic acid. DE-C-2 323 328 describes the separation of acrylic acid from an aqueous butanol/acrylic acid esterification waste liquor by extraction with a special mixture of organic solvents.

The disadvantage of the processes described above is that the organic solvent used for the extraction or absorption is separated off again in a further process stage, such as a rectification under high thermal stress. This gives rise to the danger of polymerization of the acrylic acid.

JP-A-07 082 210 describes a process for purifying acrylic acid which, in addition to acrylic acid contains acetic acid, propionic acid, acrolein and furfural. In this process, a crystallization is carried out under reduced pressure after the addition of water, a purity of 99.6% being achieved after isolation and washing of the acrylic acid crystals. Japanese Patent 45-32417 discloses a process in which an aqueous acrylic acid solution which additionally contains acetic acid and propionic acid is extracted with heptane or toluene, and water is then removed from the extract by distillation. In the next stage, the remaining extract is cooled to −20 to −80° C. in order to induce crystallization of acrylic acid. The crystals are isolated and the mother liquor is recycled to the extraction process. According to this patent, the use of an organic solvent or extracting agent is necessary since otherwise the solution, if it is cooled, solidifies without crystals being precipitated. The disadvantage of this process, apart from the addition of an organic solvent, is that a distillation has to be carried out to separate off water. Canadian Patent 790 625 relates to a further purification process of crude acrylic acid by fractional crystallization. There, the temperature is not reduced below the peritectic temperature of the acrylic acid/propionic acid system where propionic acid is the main impurity in the crude acrylic acid, while the temperature is not reduced below the eutectic temperature of the acrylic acid/acetic acid system where acetic acid is the main impurity. The acrylic acid used for crystallization is prepared here by conventional processes, for example by gas-phase oxidation of propene or acrolein, and then subjected to a preliminary purification by conventional known methods, e.g. extraction. According to the patent, the crystallization of the acrylic acid is preferably carried out essentially in the absence of water.

EP-A-0 616 998 describes a process for purifying acrylic acid by means of a combination of dynamic and static crystallization, the starting material used being prepurified acrylic acid, for example acrylic acid prepurified by distillation.

The common feature of the processes described in the above documents is that they require a preliminary purification of the acrylic acid before the crystallization. Since organic solvents are generally used in the preliminary purification and are subsequently separated off again under high thermal stress, the problem of undesired polymerization of the acrylic acid is always present here.

EP-A-0 002 612, which relates to a process for purifying acrylic acid present in aqueous solution by fractional crystallization, discloses the addition of salts to the acrylic acid solution in order to break the water/acrylic acid eutectic mixture which contains 63% by volume of acrylic acid.

EP-A-0 675 100 describes a process for the preparation of α,β-unsaturated $C_3$–$C_6$-carboxylic acids, e.g. acrylic acid, by oxidative dehydrogenation of the corresponding saturated $C_3$–$C_6$-carboxylic acid followed by crystallization of the melt with subsequent fractional distillation or followed by fractional distillation with subsequent crystallization of the melt. It is an object of the present invention to provide a process from which acrylic acid is obtained in high purity without expensive process stages.

We have found that this object is achieved and that, surprisingly, acrylic acid from a gaseous product mixture which is subjected to a condensation can be crystallized directly from the solution formed in the condensation. We have found in particular that no further purification stage and no addition of assistants are required for this purpose.

The present invention therefore relates to a process for the preparation of acrylic acid by:

(a) preparation of a gaseous product mixture which essentially has the composition of a reaction mixture of catalytic gas-phase oxidation of $C_3$-alkanes, $C_3$-alkenes, $C_3$-alkanols and/or $C_3$-alkanals and/or precursors thereof to acrylic acid, which comprises (b) condensation of the gaseous product mixture, (c) crystallization of the acrylic acid from the solution obtained in stage (b), with partial evaporation of the solution under reduced pressure, (d) isolation of the resulting crystals from the mother liquor, (e) recycling of at least a part of the mother liquor from stage (d) to stage (b) and (f) recycling of at least a part of the evaporated solution from stage (c) to stage (b).

In a preferred embodiment, the condensation in stage (b) is carried out in a column. Further preferred embodiments of the invention are evident from the following description, the subclaims, the figure and the example.

In the novel process, the acrylic acid is crystallized directly, without further intermediate or purification stages and without the addition of assistants, from the solution formed in the condensation of the product mixture. This product mixture essentially has the composition of reaction product formed in the catalytic gas-phase oxidation to give the acid.

The single figure shows a preferred embodiment for carrying out the novel process.

Here, the terms high boiler, medium boiler and low boiler and corresponding adjectival terms denote compounds/substances which have a boiling point higher than that of acrylic acid (high boilers) or those which have a boiling point which is roughly the same as that of acrylic acid (medium boilers) or those which have a boiling point lower than that of acrylic acid (low boilers).

Stage (a)

A gaseous-product mixture which essentially has the composition of a reaction mixture of the catalytic gas-phase oxidation of $C_3$-alkanes, $C_3$-alkenes, $C_3$-alkanols and/or $C_3$-alkanals and/or precursors thereof to acrylic acid is prepared in stage (a). Particularly advantageously, the gaseous product mixture is prepared by catalytic gas-phase oxidation of propene, propane or acrolein. All precursors of the abovementioned $C_3$ compounds in which the actual $C_3$ starting compound is formed as a precursor only during the gas-phase oxidation can be used as starting compounds. Acrylic acid can be prepared directly from propane.

The catalytic gas-phase reaction of propene and/or acrolein with molecular oxygen to give acrylic acid by known processes, in particular as described in the abovementioned publications, is particularly advantageous. Here, temperatures of from 200 to 450° C. and, if required, superatmospheric pressure are preferably employed. Preferably used heterogeneous catalysts are oxidic multicomponent catalysts based on the oxides of molybdenum, bismuth and iron in the 1st stage (oxidation of propene to acrolein) and on the oxides of molybdenum and vanadium in the 2nd stage (oxidation of acrolein to acrylic acid). These reactions are carried out, for example, in one stage or two stages. If the starting material used is propane, it can be converted into a propene/propane mixture by: catalytic oxydehydrogenation as described, for example, in Catalysis Today 24 (1995), 307–313 or U.S. Pat. No. 5,510,558; by homogeneous oxydehydrogenation, as described, for example, in CN-A-1 105 352; or by catalytic dehydrogenation, as described, for example, in EP-A-0 253 409, DE-A-195 08 558, EP-A-0 293 224 or EP-A-0 117 146. Suitable propene/propane mixtures are also refinery propene (70% of propene and 30% of propane) or cracker propene (95% of propene and 5% of propane). In principle, propene/propane mixtures such as the abovementioned ones can be oxidized with oxygen or air or a mixture of oxygen and nitrogen of any composition to give acrolein and acrylic acid. When a propene/propane mixture is used, propane acts as a diluent gas and/or reactant. A suitable process is also described in EP-B-0 608 838, in which propane as a reactant is converted directly into acrylic acid.

The conversion of propene into acrylic acid is highly exothermic. The reaction gas, which, in addition to the starting materials and products advantageously contains an inert diluent gas, e.g. circulating gas, atmospheric nitrogen, one or more saturated $C_1$–$C_6$-hydrocarbons, in particular methane and/or propane, and/or steam, can therefore absorb only a small part of the heat of reaction. Although the type of reactors used is not subject to any restriction per se, tube-bundle heat exchangers which are filled with the oxidation catalyst are generally used since, in said heat exchangers, the predominant part of the heat evolved in the reaction can be removed by convection and radiation to the cooled tube walls.

In the catalytic gas-phase oxidation, a gaseous mixture which, in addition to the acrylic acid, may contain essentially unconverted acrolein and/or propene, steam, carbon monoxide, carbon dioxide, nitrogen, propane, oxygen, acetic acid, propionic acid, formaldehyde, further aldehydes and maleic anhydride as byproducts is obtained instead of pure acrylic acid. Usually, the reaction product mixture contains from 1 to 30% by weight of acrylic acid, from 0.05 to 1% by weight of propene and from 0.05 to 1% by weight of acrolein, from 50 to 98% by weight of inert diluent gases, from 0.05 to 10% by weight of oxygen, from 0.05 to 2% by weight of acetic acid, from 0.01 to 2% by weight of propionic acid, from 0.05 to 1% by weight of formaldehyde, from 0.05 to 2% by weight of aldehydes and from 0.01 to 0.5% by weight of maleic anhydride, based in each case on the total reaction mixture. In particular, saturated $C_1$–$C_6$-hydrocarbons, such as from 0 to 90% by weight of methane and/or propane, as well as from 1 to 30% by weight of steam, from 0.05 to 15% by weight of carbon oxides and from 0 to 90% by weight of nitrogen, based in each case on 100% by weight of diluent gas, are contained as inert diluent gases.

Stage (b)

In stage (b), the reaction product obtained in stage (a) is subjected to a condensation, in particular a partial or total condensation, a solution being obtained.

The condensation is preferably carried out in a column. Here, a column having baffles which effect separation, in particular having packings and/or trays, preferably bubble trays, sieve trays, valve trays and/or dual-flow trays, is used. The condensable components of the gaseous product mixture from stage (a) are condensed as fractions by cooling. Since, owing to the impurities and diluent gases, the gas mixture contains a high boiler, medium boiler and low boiler fraction and uncondensable components, one or more side take-offs can be provided at the appropriate points in the column. In contrast to a conventional condensation, a condensation in a column thus permits separation into the individual components. Suitable columns comprise at least one cooling apparatus, for which all conventional heat transfer apparatuses or heat exchangers in which the heat formed in the condensation is removed indirectly (externally) are suitable. Tube-bundle heat exchangers, plate-type heat exchangers and air coolers are preferred. Suitable cooling media are air in the corresponding air coolers and cooling liquids, in particular water, in other cooling apparatuses. If only one cooling apparatus is provided, it is installed at the top of the column in which the low boiler fraction is condensed. Since the acrylic acid-containing gas mixture contains a plurality of fractions, it is expedient to install a plurality of cooling apparatuses in various sections of the column, for example a cooling apparatus in the lower section of the column for condensing the high boiler fraction and a cooling apparatus at the top of the column for condensing the low boiler fraction. The fraction containing the acrylic acid is removed in the middle part of the column, via one or more side take-offs. The pressure present in the column depends on the amount of uncondensable components and is preferably 0.5–5, in particular 0.8–3, bar absolute pressure. The exact operating conditions for the column, such as temperature and pressure, connection and arrangement of the cooling apparatus(es), arrangement of the side take-off/side take-offs for removing acrylic acid, choice of the column height and of the column diameter, number and spacing of the baffles/trays effecting separation in the column or type of column baffles effecting separation, can be determined by a person skilled in the art in experiments customary in the field, depending on the separation task. In a preferred embodiment, the hot gas mixture is cooled directly or indirectly before the condensation. In the case of direct cooling, it is preferable if the gas mixture is cooled with the aid of the high boiler fraction condensed from the gas mixture. In another case, an assistant is introduced into the process but has to be worked up again. In terms of apparatus, this preliminary cooling can be integrated in the bottom region of the column (with or without column baffles) or can be separated from the column in a separate apparatus, for example a gas cooler, a quench apparatus or a flash pot. In a particularly preferred embodiment of the invention, the condensation of the gaseous reaction mixture takes place in a column as follows, it being possible to organize the column in various sections in which the following different process functions are performed:

1. Bottom region: Cooling of the hot gas mixture

The hot gas mixture is passed into the bottom region and cooled. This can be effected by indirect cooling, for example by means of a heat exchanger, or by direct cooling with, as the cooling medium, high boiler fraction condensed in the next section of the column.

2. First cooling loop: Condensation of the high boiler fraction

In the region of the first cooling loop, the heat of condensation is removed externally via the first cooling loop by means of a heat exchanger with, for example, water as cooling medium, by removing condensed high boiler fraction from the column, cooling said fraction by means of the heat exchanger and recycling a part of the cooled, condensed, high boiler fraction to the column while the other part, usually less than 1% by weight, based on 100% by weight of condensate, in a side take-off, is removed. The recycled, condensed high boiler fraction is fed countercurrent to the ascending gas.

3. First cooling loop to side take-off: High boiler concentration

Between the first cooling loop and the side take-off, distillative concentration and condensation of the high boiler fraction from the gas stream fed countercurrent upward are effected toward the first cooling loop.

4. Side take-off Removal of the acid

Acrylic acid is removed via the side take-off.

5. Side take-off to second cooling loop Concentration of the medium boiler fraction In the region between the side take-off and the second cooling loop, the medium boiler fraction from the gas stream fed countercurrent upward is concentrated, the medium boiler fraction being concentrated toward the side take-off.

6. Second cooling loop Condensation of the low boiler fraction

In the region of the second cooling loop, the low boiler fraction from the gas stream fed countercurrent upward is condensed. The heat of condensation is removed externally via the second cooling loop by means of a heat exchanger with, for example, water as cooling medium, by removing condensed low boiler fraction and cooling it and recycling a part of the cooled, condensed low boiler fraction to the column while the other part is removed. The uncondensed components, which are preferably nitrogen, carbon monoxide, carbon dioxide, oxygen, methane, propane and propene, are removed from the top of the column.

In addition, the condensation can be carried out by conventional methods in one stage or a plurality of stages, the type of condensation not being subject to any particular restriction. Advantageously, the condensation is carried out using a direct condenser, condensate already produced being brought into contact with the hot gaseous reaction product. Suitable apparatuses for condensation are in particular spray scrubbers, Venturi scrubbers, bubble columns or apparatuses having sprayed surfaces.

The mixture obtained by partial or total condensation of the reaction product from stage (a), in particular the condensate of the medium boiler fraction in the case of condensation in a column, preferably contains from 60 to 99.5% by weight of acrylic acid, from 0.1 to 40% by weight of water and in addition from 0.1 to 15% by weight of impurities, in particular, based in each case on 100% by weight of condensate, from 0.01 to 5% by weight of acrolein, from 0.05 to 5% by weight of acetic acid, from 0.01 to 5% by weight of propionic acid, from 0.01 to 5% by weight of formaldehyde, from 0.01 to 5% by weight of further aldehydes and from 0.01 to 5% by weight of maleic acid. Particularly preferably, a mixture which contains from 85 to 98% by weight of acrylic acid, from 0.5 to 14% by weight of water and in addition from 0.5 to 5% by weight of impurities, in particular, based in each case on 100% by weight of condensate, from 0.01 to 3% by weight of acrolein, from 0.1 to 3% by weight of acetic acid, from 0.01 to 3% by weight of propionic acid, from 0.01 to 3% by weight of formaldehyde, from 0.01 to 3% by weight of further aldehydes and from 0.01 to 3% by weight of maleic acid, is obtained in the condensation.

Stage (c)

In stage (c), the solution obtained in stage (b) and having a higher acrylic acid concentration is crystallized. Thus, the solution obtained in the condensation stage is fed directly to the crystallization. The crystallization can be carried out continuously or batchwise, in one stage or a plurality of stages. Preferably, the crystallization is effected in one stage. All crystallization methods in which the crystallized solution/melt is thoroughly mixed by stirring or circulation are suitable, both continuous and batchwise procedures. Preferably used apparatuses are stirred kettle crystallizers and forced circulation crystallizers but draught-tube and fluidized-bed crystallizers may also be used.

According to the invention, the solution is partly evaporated in the crystallization. The crystallizing solution features the boiling point which is dependent on the pressure in the crystallization. The pressure in the crystallization is brought to the desired value by means of an apparatus for generating reduced pressure. Said apparatus is not subject to any restriction here. All systems which reach the desired reduced pressure in one stage or a plurality of stages by mechanical and/or thermal compression are suitable. Liquid ring pumps, in particular in combination with vapor-jet pumps, vapor-jet pumps alone or Roots pumps or rotary vane pumps are preferably used. The pressures to be established are dependent on the composition of the crystallizing solution. They are expediently from 1 to 15, preferably from 3 to 8, mbar (absolute).

Advantageously, the temperature of the solution during crystallization is from −10 to +14° C., in particular from −5 to +10° C. The crystallization is advantageously operated so that a solids content of from 5 to 60 g of solid per 100 g of suspension is established, contents of from 15 to 45 g of solid per 100 g of suspension being preferred.

Stage (d)

In stage (d), the acrylic acid crystals obtained in stage (c) are separated from the mother liquor. All known solid-liquid separation methods are suitable for this purpose. In a preferred embodiment of the invention, the crystals are separated from the mother liquor by filtration and/or centrifuging. Advantageously, the filtration or centrifuging is preceded by preliminary thickening of the suspension, for example by hydrocyclone(s). All known centrifuges which operate batchwise or continuously are suitable for the centrifuging. Reciprocating centrifuges which can be operated in one stage or a plurality of stages are most advantageous. Helical-screen centrifuges or helical-conveyor centrifuges (decanters) are also suitable. Filtration is advantageously effected by means of suction filters, which are operated batchwise or continuously, with or without a stirrer, or by means of belt filters. In general, the filtration can be carried out under superatmospheric or reduced pressure.

Further process steps for increasing the purity of the crystals or the crystal cake can be provided during and/or after the solid-liquid separation. In a particularly advantageous embodiment of the invention, the separation of the crystals from the mother liquor is followed by one-stage or multistage washing and/or sweating of the crystals or of the crystal cake. During the washing, the amount of wash liquid is suitably from 0 to 500, preferably from 30 to 200, g of wash liquid/100 g of crystals. The wash liquid used is not subject to any restriction. However, washing is advantageously carried out using pure product, i.e. using a liquid which contains acrylic acid whose purity is higher than that of the crystal cake to be washed, but at least purer than the mother liquor in the crystallization. Washing with water is also possible. The washing can be effected in apparatuses suitable for this purpose. Wash columns in which the separation of the mother liquor and the washing are effected in one apparatus, centrifuges which can be operated in one stage or a plurality of stages or suction filters or belt filters are advantageously used. The washing can be carried out on centrifuges or belt filters in one stage or a plurality of stages. Here, the wash liquid can be fed countercurrent to the crystal cake.

Sweating comprises local melting of contaminated regions. Advantageously, from 0 to 100 g of crystals are melted during the sweating per 100 g of crystals before the sweating, preferably from 5 to 35 g of crystals are melted per 100 g of crystals. The sweating is particularly preferably carried out on centrifuges or belt filters. It may also be suitable to carry out a combination of washing and sweating in one apparatus.

The acrylic acid crystals after the solid-liquid separation and any further washing and/or sweating constitute the purified acid from the process. The purity of the crystals obtained is as a rule from 97 to 99.9, in particular from 98.5 to 99.9, % by weight of acrylic acid. The crystals prepared by the novel process now contain only very small amounts of impurities, such as acetic acid, maleic acid or aldehydes.

If desired, the purified acid can be esterified by known methods or further purified by known methods.

Stage (e)

In stage (e), the mother liquor from stage (d), which remains behind after isolation of the crystals, is at least partly recycled directly to the condensation stage (b). The amount of recycled mother liquor is from 0 to 100, in particular from 80 to 100, preferably 100, % by weight. If the condensation is carried out in a column, the mother liquor is expediently recycled to below the side take-off of the column, preferably in the region between the first cooling loop and the side take-off, most preferably in the region just below or a few trays below the side take-off of the column.

Stage (f)

In stage (f), at least a part of the solution evaporated in stage (c) is recycled to the condensation stage (b). The amount of solution recycled to stage (b) is from 0 to 100, in particular from 50 to 100, preferably from 80 to 100, most preferably about 100, % by weight. If the condensation is carried out in a column, the evaporated solution is expediently recycled to above the side take-off of the column, preferably in the region between the side take-off and the second cooling loop, most preferably in the region just above or a few trays above the side take-off of the column. That part of the evaporated solution which is not recycled to stage (b) is advantageously recycled to the crystallization stage (c). It is also possible to remove evaporated solution, expediently not more than 80% by weight of the evaporated solution being removed.

The recycling of the evaporated solution to (b) and, if required, stage (c) is not subject to any restriction at all with regard to the phase state (gaseous, partly condensed, completely condensed). The recycling is preferably effected in the liquid state after carrying out a partial or total condensation of the evaporated solution. Here, the condensation methods and apparatuses and the production of the mass-transfer and heat-exchange surfaces required for the condensation are not subject to any restriction at all. The exchange surface(s) may be in the form of conventional surface condensers, such as tube-bundle condensers or plate-type heat exchangers. The exchange surfaces are however preferably formed by spraying liquids, for example already obtained condensate and/or by trickling appropriate liquid or causing it to flow over apparatus surfaces and/or baffles and/or packings. Here, it is possible to mix a liquid removed from a suitable point in the process with the condensate and to use this mixture for producing the exchange surface. The liquid to be mixed with the condensate is expediently chosen so that the resulting mixture has a lower freezing point than the condensate itself. Depending on the composition of the vapor removed in the crystallization (c), suitable points for withdrawing mixing liquid when carrying out the condensation stage (b) in a column may be side take-offs of the column or liquid/suspension side take-offs from stage (c) and (d). Acrylic acid purified by crystallization or water supplied from outside are also possible as mixing liquid. Preferably at least 90%, in particular at least 95%, of the evaporated solution are condensed. Most preferably, the total condensable amount of the evaporated solution is condensed. Uncondensable fractions of the evaporated solution are expediently removed via the apparatus for reduced pressure generation in stage (c). In addition to the partial or total condensation of the evaporated solution, it is also possible to recycle the evaporated solution in gaseous form to stage (b), which however is more expensive owing to the compressors or pumps required.

It is also possible to introduce components or mixtures which have a lower boiling point than that of acrylic acid at a suitable point into the crystallization (c) or into stages connected with it, in order that the reduced pressure required for a desired crystallization temperature does not have to be so low. Suitable points here are the crystallization stage (c) itself and its feed stream arriving from stage (b) and the stage (f) in the case of partial recycling of the evaporated solution to stage (c). More preferable, however, is the separation stage (d) with at least partial recycling of the mother liquor from stage (d) to stage (c), since the components or mixtures which have a lower boiling point than that of acrylic acid can then simultaneously be used as wash liquid. When condensation stage (b) is carried out in a column, suitable components or mixtures having a lower boiling point than that of acrylic acid are corresponding fractions from side take-offs of the column or streams fed in from outside, e.g. water.

The figure shows a preferred embodiment for carrying out the novel process. Air is fed to the synthesis reactors 4 and 5 via line 2 and compressor 3. In addition, recycle gas compressed by compressor 6 and essentially consisting of nitrogen, carbon oxides and unconverted starting materials, and propene originating from line 1, are fed to the reactor 4 via line 9. The first stage of the two-stage gas-phase oxidation, i.e. the oxidation of propene to acrolein, takes place in synthesis reactor 4. In synthesis reactor 5, the acrolein is then oxidized to the corresponding acid. A gaseous product mixture which, in addition to the acid, contains further, abovementioned impurities is formed here. Said product mixture is fed via line 7 to the condenser 8, in which it is cooled and condensed. The condenser 8 is in the form of a column in the figure. The uncondensed part of the product mixture is removed via line 9, a part thereof being recycled as recycle gas, as described above, to reactor 4 and the other part, preferably 50% of the total stream of line 9, being removed as waste gas from the plant via line 10. The condensed high boiler fraction is removed via line 18 while the condensed low boiler fraction is removed via line 19. The condensed medium boiler fraction, which contains the major part of the acrylic acid, is fed via line 11 (side take-off) to the crystallization apparatus 12 in which the crystallization is carried out. The mother liquor from the crystallization is fed together with the crystals via line 13 to a suitable apparatus 14 for solid-liquid separation, the crystals being removed via line 15 and the mother liquor via line 16. At least a part of the mother liquor is fed via line 17 into the condenser 8, preferably below the side take-off (line 11) and thus fed back to the condensation. The purified acid is thus removed via line 15. In the crystallization apparatus 12, a part of the solution is evaporated under reduced pressure which is generated by the apparatus 25 for generating reduced pressure, and said part is fed via line 21 to the condensation apparatus 20. In this, the evaporated solution is virtually completely converted into the condensed phase. The condensed phase is partly recycled via line 22 to the crystallization apparatus 12 and partly fed via line 23 to the condensation apparatus 8, preferably above the side take-off (line 11). Those fractions of the evaporated solution which are not condensed in the apparatus 20 are fed via line 24 to the apparatus 25 and are removed therefrom, and from the process, via line 26 as waste gas.

By recycling mother liquor and, preferably condensed, vapors to the condensation stage, the present invention permits high yield. The heat evolved in the crystallization stage is removed from the crystallization in a simple manner by evaporating some of the solution. At the same time, a part of the work required for separating acrylic acid and low boilers (in comparison with acrylic acid) is performed by evaporating some of the solution in the crystallization.

Compared with the processes known to date, the novel process has the further advantage that, after condensation of the product mixture formed in the gas-phase oxidation, an acid of very good quality is obtained by crystallization directly from the solution formed in the condensation. With the use of a crystallization comprising more than one purification stage, pure acid can be produced directly, no preliminary purification being necessary, in contrast to the abovementioned publications, Canadian Patent 790 625, JP-A-0 07 082 210-A and EP-A-0 616 998.

A further important advantage of the novel process is that the process is carried out at relatively low temperatures, i.e. the main stream of acrylic acid is removed from the process as product directly via condensation and crystallization. Since, in contrast to the prior art, no assistant is added and hence no high thermal load (in particular in the case of high acrylic acid contents) is required for separating off the assistant, polymerization problems and the use of process stabilizers, as encountered here in the prior art, are reduced. Moreover, this also avoids or reduces fouling. It is surprising that -acrylic acid solutions obtained by gas-phase oxidation and condensation can be directly crystallized and that products of very high purity are obtained thereby. In particular, it was surprising that this is also possible in the case of aqueous condensates.

The following example, which represents a preferred embodiment of the invention, illustrates the invention.

Example

The following mixture at a temperature of 270° C. was obtained from reaction stage (a) by catalytic gas-phase oxidation of propene.

TABLE 1

| Component | Concentration in % by weight |
| --- | --- |
| Water | 4.4 |
| Formaldehyde | 0.2 |
| Acetic acid | 0.4 |
| Acrylic acid | 10.1 |
| Maleic anhydride | 0.07 |
| Benzoic acid | 0.02 |
| Acrolein | 0.1 |
| Phthalic anhydride | 0.01 |
| Propionic acid | 0.002 |
| Maleic acid | 0 |
| Allyl acrylate | 0.001 |
| Benzaldehyde | 0.0005 |
| Furfural | 0.0015 |
| Phenothiazine | 0 |
| Nitrogen | 76.5 |

TABLE 1-continued

| Component | Concentration in % by weight |
| --- | --- |
| Oxygen | 3.6 |
| Carbon monoxide | 0.7 |
| Carbon dioxide | 2.6 |
| Propene | 0.5 |
| Propane | 0.7 |

The mixture (10867 g/h) was fed to the condensation stage (b). The condensation apparatus used was a tray column having 27 bubbles trays. The temperature in the bottom of the column was 100° C. The heat of condensation was removed via heat exchangers at trays 1 and 27. Above the side take-off of the column, phenothiazine was added as a stabilizer. At tray 27, a stream of 269 g/h having the following composition was taken off:

TABLE 2

| Component | Concentration in % by weight |
| --- | --- |
| Water | 89.3 |
| Formaldehyde | 0.075 |
| Acetic acid | 9.5 |
| Acrylic acid | 1.1 |
| Maleic anhydride | 0 |
| Benzoic acid | 0 |
| Acrolein | 0.028 |
| Phthalic anhydride | <0.0001 |
| Propionic acid | <0.0001 |
| Maleic acid | <0.0001 |
| Allyl acrylate | <0.0001 |
| Benzaldehyde | <0.0001 |
| Furfural | <0.0001 |
| Phenothiazine | <0.0001 |
| Nitrogen | 0 |
| Oxygen | 0 |
| Carbon monoxide | 0 |
| Carbon dioxide | 0 |
| Propene | 0 |
| Propane | 0 |

At the bottom of the column, a stream of 17.8 g/h having the following composition was taken off:

TABLE 3

| Component | Concentration in % by weight |
| --- | --- |
| Water | 1.3 |
| Formaldehyde | 0.0033 |
| Acetic acid | 0.9 |
| Acrylic acid | 33.1 |
| Maleic anhydride | 40.3 |
| Benzoic acid | 12.2 |
| Acrolein | 0.01 |
| Phthalic anhydride | 6.1 |
| Propionic acid | 0.045 |
| Maleic acid | <0.0001 |
| Allyl acrylate | 0.02 |
| Benzaldehyde | 0.3 |
| Furfural | 0.5 |
| Phenothiazine | 5.2 |
| Nitrogen | 0 |
| Oxygen | 0 |
| Carbon monoxide | 0 |
| Carbon dioxide | 0 |
| Propene | 0 |
| Propane | 0 |

At tray 11, a liquid stream of 4955 g/h at 95° C. was taken off from the column and was then crystallized. This stream had the following composition:

TABLE 4

| Component | Concentration in % by weight |
| --- | --- |
| Water | 1.5 |
| Formaldehyde | 0.005 |
| Acetic acid | 6 |
| Acrylic acid | 91.5 |
| Maleic anhydride | 0.6 |
| Benzoic acid | <0.0001 |
| Acrolein | 0.011 |
| Phthalic anhydride | <0.0001 |
| Propionic acid | 0.069 |
| Maleic acid | <0.0001 |
| Allyl acrylate | 0.2 |
| Benzaldehyde | 0.001 |
| Furfural | 0.1 |
| Phenothiazine | 0.016 |
| Nitrogen | 0 |
| Oxygen | 0 |
| Carbon monoxide | 0 |
| Carbon dioxide | 0 |
| Propene | 0 |
| Propane | 0 |

The mixture originating from tray 11 was then crystallized in a 10 l stirred container with a helical ribbon agitator. The heat of crystallization was removed by partial evaporation. The crystallization temperature of the solution was 6.5° C. The pressure was 3 mbar. The suspension produced during the crystallization was separated into crystals and mother liquor on a centrifuge at 2000 rpm (centrifuge diameter 250 mm) and in a centrifuging time of 1 minute. The crystals (1486 g/h) were then washed with melted crystals (323 g/h) for 1 min at 2000 rpm.

The mother liquor was recycled together with the wash liquid to tray 10 of the condensation column (3060 g/h). The solution evaporated in the crystallization was recycled to tray 15 of the column after condensation (732 g/h). The composition of this stream was:

TABLE 5

| Component | Concentration in % by weight |
| --- | --- |
| Water | 6.7 |
| Formaldehyde | 0.034 |
| Acetic acid | 14.2 |
| Acrylic acid | 78.1 |
| Maleic anhydride | 0.1 |
| Benzoic acid | <0.0001 |
| Acrolein | 0.072 |
| Phthalic anhydride | <0.0001 |
| Propionic acid | 0.069 |
| Maleic acid | <0.0001 |
| Allyl acrylate | 0.4 |
| Benzaldehyde | <0.0001 |
| Furfural | 0.069 |
| Phenothiazine | 0 |
| Nitrogen | 0 |
| Oxygen | 0 |
| Carbon monoxide | 0 |
| Carbon dioxide | 0 |
| Propene | 0 |
| Propane | 0 |

Analysis of the crystals gave the following composition:

TABLE 6

| Component | Concentration in % by weight |
| --- | --- |
| Water | 0.026 |
| Formaldehyde | 0 |

TABLE 6-continued

| Component | Concentration in % by weight |
|---|---|
| Acetic acid | 0.8 |
| Acrylic acid | 99.1 |
| Maleic anhydride | 0.04 |
| Benzoic acid | 0 |
| Acrolein | 0 |
| Phthalic anhydride | 0 |
| Propionic acid | 0.02 |
| Maleic acid | 0 |
| Allyl acrylate | 0.01 |
| Benzaldehyde | <0.0001 |
| Furfural | 0.007 |
| Phenothiazine | 0.003 |
| Nitrogen | 0 |
| Oxygen | 0 |
| Carbon monoxide | 0 |
| Carbon dioxide | 0 |
| Propene | 0 |
| Propane | 0 |

As shown in Table 6, the novel process permits the preparation of pure acrylic acid.

We claim:

1. A process for the preparation of acrylic acid by:
   (a) preparation of a gaseous product mixture which essentially has the composition of a reaction mixture of catalytic gas-phase oxidation of $C_3$-alkanes, $C_3$-alkenes, $C_3$-alkanols and/or $C_3$-alkanals and/or precursors thereof to acrylic acid,
   which comprises
   (b) condensation of the gaseous product mixture,
   (c) crystallization of the acrylic acid from the solution obtained in stage (b), with partial evaporation of the solution under reduced pressure,
   (d) isolation of the resulting crystals from the mother liquor,
   (e) recycling of at least a part of the mother liquor from stage (d) to stage (b) and
   (f) recycling of at least a part of the evaporated solution from stage (c) to stage (b).

2. A process as claimed in claim 1, wherein the crystals in stage (d) are separated from the mother liquor by filtration and/or centrifuging.

3. A process as claimed in claim 1, wherein the crystals isolated in stage (d) are subjected to at least one washing and/or sweating procedure.

4. A process as claimed in claim 1, wherein, in stage (e) from 80 to 100% by weight of the mother liquor from stage (d) are recycled to stage (b).

5. A process as claimed in claim 1, wherein, in stage (f), from 50 to 100% by weight of the evaporated solution from stage (c) are recycled to stage (b).

6. A process as claimed in claim 5, wherein that part of the evaporated solution which is not recycled to stage (b) is recycled to stage (c).

7. A process as claimed in claim 1, wherein at least 90% by weight of the evaporated solution from stage (c) are condensed before recycling to stage (b) and, if required, stage (c).

8. A process for the preparation of acrylic acid by:
   (a) preparation of a gaseous product mixture which essentially has the composition of a reaction mixture of catalytic gas-phase oxidation of $C_3$-alkanes, $C_3$-alkenes, $C_3$-alkanols and/or $C_3$-alkanals and/or intermediates thereof to acrylic acid, which comprises
   (b) condensation of the gaseous product mixture,
   (c) crystallization of the acrylic acid from the solution obtained in stag (b) with partial evaporation of the solution under reduced pressure,
   (d) isolation of the resulting crystals from the mother liquor,
   (e) recycling of at least a part of the mother liquor from stage (d) to stage (b) and
   (f) recycling of at least a part of the evaporated solution from stage (c) to stage (b),
   wherein the condensation in stage (b) is carried out in a column having baffles which effect separation.

9. A process as claimed in claim 11, wherein, in the condensation, the solution to be crystallized in stage (c) is removed as the medium boiler fraction from the column.

10. A process as claim 8, wherein the crystallization in stage (c) is carried out at from 1 to 15 mbar (absolute) and at from −10 to +14° C.

11. A process as claimed in claim 8, wherein the crystals in stage (d) are separated from the mother liquor by filtration and/or centrifuging.

12. A process as claimed in claim 8, wherein the crystals isolated in stage (d) are subjected to at least one washing and/or sweating procedure.

13. A process as claimed in claim 8, wherein, in stage (e), from 80 to 100% by weight of the mother liquor from stage (d) are recycled to stage (b).

14. A process as claimed in claim 8, wherein, in stage (f), from 50 to 100% by weight of the evaporated solution from stage (c) are recycled to stage (b).

15. A process as claimed in claim 14, wherein that part of the evaporated solution which is not recycled to stage (b) is recycled to stage (c).

16. A process as claimed in claim 8, wherein at least 90% by weight of the evaporated solution from stage (c) are condensed before recycling to stage (b) and, if required, stage (c).

17. A process for the preparation of acrylic acid by:
   (a) preparation of a gaseous product mixture which essentially has the composition of a reaction mixture of catalytic gas-phase oxidation of $C_3$-alkanes, $C_3$-alkenes, $C_3$-alkanols and/or $C_3$-alkanals and/or intermediates thereof to acrylic acid, which comprises
   (b) condensation of the gaseous product mixture,
   (c) crystallization of the acrylic acid from the solution obtained in stage (b), with partial evaporation of the solution under reduced pressure,
   (d) isolation of the resulting crystals from the mother liquor,
   (e) recycling 80 to 100% by weight of the mother liquor from stage (d) to stage (b) and
   (f) recycling 50 to 100% by weight of the evaporated solution from stage (c) to stage (b).

18. A process as claimed in claim 17, wherein that part of the evaporated solution which is not recycled to stage (b) is recycled to stage (c).

19. A process as claimed in claim 17, wherein at least 90% by weight of the evaporated solution from stage (c) are condensed before recycling to stage (b) and, if required, stage (c).

20. A process as claimed in claim 1, wherein the crystallization in stage (c) is carried out at from 1 to 15 mbar (absolute) and at from −10 to +14° C.

* * * * *